United States Patent [19]

Schütz

[11] Patent Number: 4,483,674

[45] Date of Patent: Nov. 20, 1984

[54] DEVICE FOR ORTHODONTIC TOOTH REGULATION

[76] Inventor: Winfried Schütz, Ravensburger Ring 63, 8000 München 60, Fed. Rep. of Germany

[21] Appl. No.: 488,703

[22] Filed: Apr. 26, 1983

[30] Foreign Application Priority Data

May 7, 1982 [DE] Fed. Rep. of Germany ....... 3217243
May 28, 1982 [DE] Fed. Rep. of Germany ....... 3220240

[51] Int. Cl.$^3$ ............................................. A61C 3/00
[52] U.S. Cl. ......................................... 433/22; 433/7; 433/11; 433/18; 433/20
[58] Field of Search ...................... 433/18, 20, 2, 5, 6, 433/7, 11, 19, 21, 22, 23, 24

[56] References Cited

U.S. PATENT DOCUMENTS

| | | | |
|---|---|---|---|
| 618,105 | 1/1899 | Knapp | 433/7 |
| 632,945 | 9/1899 | Knapp | 433/23 |
| 660,194 | 10/1900 | Lukens | 433/7 |
| 2,959,856 | 11/1960 | Gurin | 433/22 |
| 3,690,003 | 9/1972 | Gerber | 433/19 |
| 3,798,773 | 3/1974 | Northcutt | 433/19 |
| 4,355,975 | 10/1982 | Fujita | 433/11 |

FOREIGN PATENT DOCUMENTS

| | | | |
|---|---|---|---|
| 1807927 | 7/1969 | Fed. Rep. of Germany | 433/7 |
| 337270 | 4/1904 | France | 433/20 |
| 166600 | 3/1934 | Switzerland | 433/20 |

Primary Examiner—John J. Wilson
Attorney, Agent, or Firm—Hayes, Davis & Soloway

[57] ABSTRACT

The invention refers to a device for orthodontic tooth regulation by means of fixed regulating appliances (Edgewise technique). Through such fixed appliances the teeth will be moved under control along a regulating archwire which is ligated to the brackets which are fixed to the teeth. In order to control the forces transmitted to the teeth to be moved and to avoid overload of the periodontal apparatus, it is proposed according to the invention to insert regulating screws along the regulating archwire between fixed parts (such as brackets or tubes) of the regulating appliance, which can be adjusted in their length. The regulating arch is preferably provided partly with a thread, to which regulating nuts can be screwed on. Using such regulating screws as force elements, the force transmitted to the teeth can be measured in a way that the teeth will be moved within a physiological frame. Treatment time for tooth regulation with such regulating screws can be reduced considerably in comparison with common methods using spring loops, coil springs or elastics.

11 Claims, 13 Drawing Figures

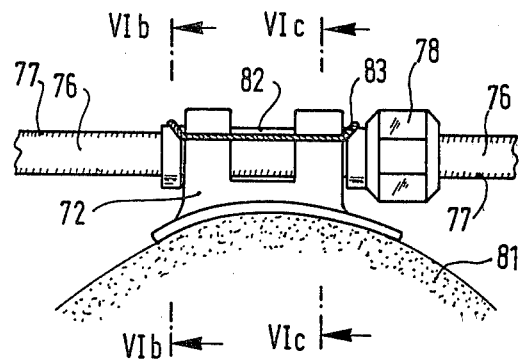
Fig. 6a
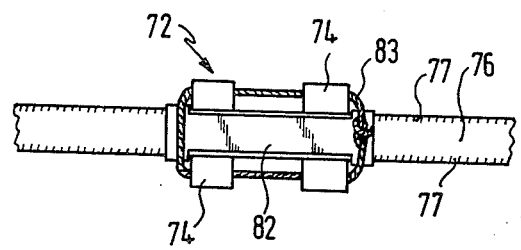
Fig. 6d
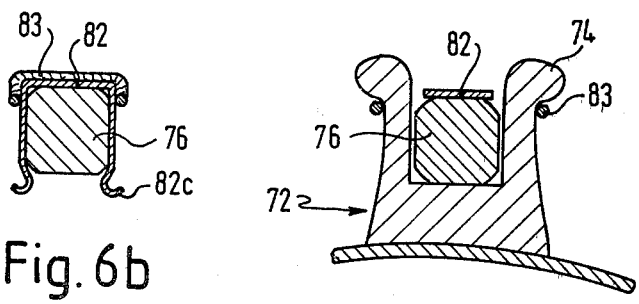
Fig. 6b
Fig. 6c
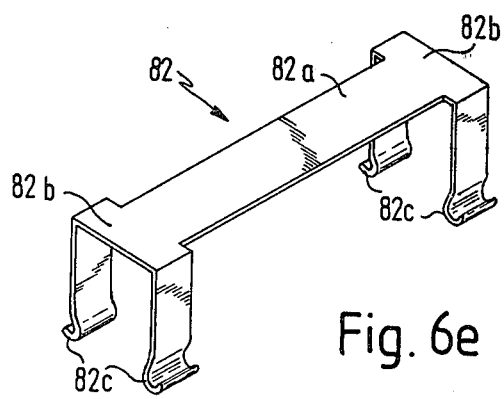
Fig. 6e

DEVICE FOR ORTHODONTIC TOOTH REGULATION

The invention refers to a device for orthodontic tooth regulation.

One of the most important aims of orthodontics is to arrange the space for the single teeth in the jaws, particularly the dentulous alveolar ridge, in such a manner that the teeth can stand correctly in the jaw or dental arch and contact each other at their desired contact points. Mainly two problems must be differentiated: deficiency and surplus of space within the dental arch. Space deficiency first of all means the necessity to make room for the teeth which they need for their correct position. This is done either by—in cases of large space deficiency—extraction with following regulation of the remaining teeth or by jaw expansion or tooth movements which mean opening of tooth gaps into which a tooth can grow or be moved. Space surplus in the form of gaps is eliminated by reducing the tooth distances.

In the main are two techniques used in orthodontics: the one technique with removable appliances and the other technique with fixed appliances. Using the orthodontic technique with fixed appliances, the teeth can be moved under total control. Such techniques are, e.g. Multi-band technique or the so-called Edgewise technique. According to this orthodontical method fixtures such as bands with tubes or brackets will be applied to the teeth which will be connected by strong leading wires or regulating edgewise arches with a crosscut up to 0.22×0.28 inches. The necessary forces for the tooth movements are produced either by the regulating arch itself or with coil springs, loops bent into the regulating arch or elastics, etc.

With the help of this orthodontical method with fixed appliances, a totally controlled, precisely in three-dimensions and movement of the tooth bodily becomes possible; however, a disadvantage is the fact that the extent of the force of the said elements, currently used, transmitted to the teeth could not be sufficiently controlled. Elastics, tension or compression springs not only have to move the teeth but also overcome the friction between the tube, the bracket and the regulating wire.

If the forces are too weak, there is no effect at all, while forces which are too heavy cause tissue damage, such as hyalinizing, root resorption or the like.

Loops for reducing toothgaps, the so-called retraction loops (e.g. Bulloops), do not have to overcome the said friction, but their activation produces peak forces which will diminish slowly over an acting period of four weeks—in relation to the tooth movement. Then they will be reactivated in other words tightened again.

Another disadvantage of this loop technique consists in the fact that the bending of the loop into the archwire—the fabrication of which needs time and its activation is difficult and sometimes causes injury—means a decrease of arch stability of the regulating wire. This can cause a partial lowering of the horizontal plane and makes another leveling arch necessary after closing the tooth gap. This is not only an additional expense of work, but also prolongs treatment time.

It is an object of the invention to develop and improve a device of said method for tooth regulation with fixed appliances in such a way that the precise control of the forces used in the controlled displacement of the tooth becomes possible.

It is a further object of the invention to simplify the regulating appliance, especially the force elements for the transmission of moving forces. Furthermore, it is the object of the invention to simplify and improve the application, the tuning and the control of the regulating appliance.

According to the invention, the force element is an adjustable regulating screw adaptable in its length which is inserted along the regulating arch between fixed parts of the regulating appliance. According to the desired regulating treatment, the regulating screw can be used either as an expension—or opening—screw in order to produce gaps, or as a retraction—or contraction—screw for closing gaps between two or more teeth. Furthermore, single tooth movements, midline discrepancy, closing of multiple gaps and transverse jaw-expansion becomes possible.

It is especially advantageous when a thread is cut in the edgewise regulating arch itself, preferably only in its corners. A regulating screw can be screwed on this thread which then contacts fixed parts of the regulating appliance, e.g. bracket arms or tubes. By adjusting this regulating screw, finely adjusted forces can be transmitted on the teeth to be moved. One advantage of this arrangement of the regulating screw inserted directly on the regulating arch is that the size increase of the whole regulating appliance is small. Besides, the edgewise cross-section of the regulating archwire stays almost the same, a fact that guarantees no loss of control over the tooth movements along the regulating arch.

An additional advantage of the invention is the time saving effect during treatment in comparison with other methods—about two months in a total treatment time of three years.

Further objects and advantages of the invention will now be described, by way of example, with reference to preferred embodiments and accompanying drawings, in which FIG. 1 is a longitudinal section through a regulating screw, in this case an expansion screw according to the invention;

FIG. 5b is a cross-section through a regulating screw shown in FIG. 5a;

FIG. 6a is another embodiment of an integrated regulating screw with a guide shoe;

FIG. 6b is a section taken on line VIb—VIb in FIG. 6a;

FIG. 6c is a section taken on line VIc—VIc in FIG. 6b;

FIG. 6d is a top view on the regulating screw shown in FIG. 6a without a regulating nut;

FIG. 6e is a view of the guide shoe in perspective.

Figure 1:
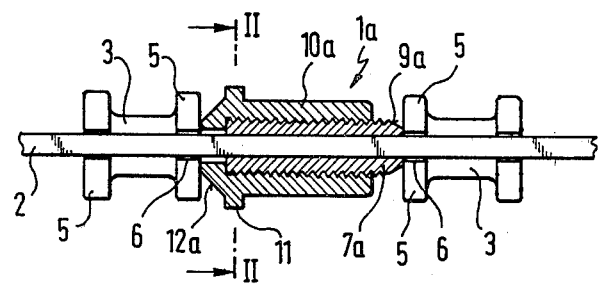
Figure 4:
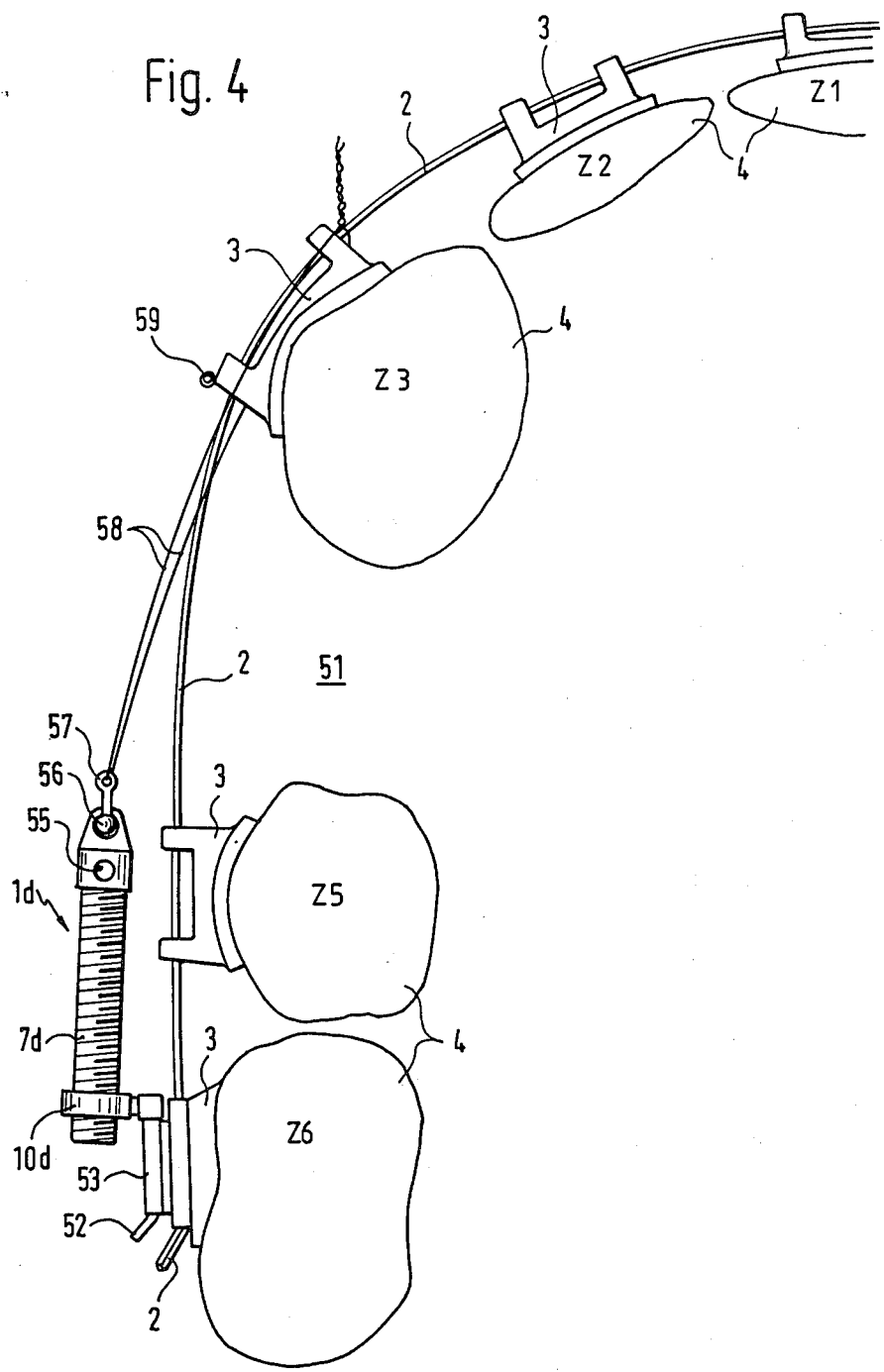
FIG. 4 is a view of a part of a fixed regulating appliance with a contraction screw according to the invention for closing of toothgaps.

In FIG. 1 an opening screw 1a, applied on an edgewise regulating arch 2 is shown, which engages two brackets 3 on a fixed regulating appliance with its both opposite ends. Part of such regulating appliances is shown in FIG. 4. The brackets will be bonded each onto a single tooth surface. From there they point outwardly from the teeth with their bracket arms or bracket wings 5. Each bracket normally has four such bracket arms, whereby between two facing bracket arms a so-called bracket slot 6 is always left free. The said edgewise regulating archwire is inserted into the slots of all the brackets. They are relatively strong with a crosscut of e.g. 0.55×0.71 (mm), that is, 0.022×0.028 inches. The bracket slot itself has a rectangular cross-section. The brackets are positioned so that the force of the regulating arch can move, e.g. tip the teeth accordingly.

FIG. 1 shows two such brackets which are arranged on adjacent teeth 4 standing too close to each other thus prohibiting another tooth to stand in its assigned position. The gaps between these two adjacent teeth has to be enlarged in order to make room or the other malpositioned tooth.

The opening screw in FIG. 1 encloses an oblong internal screw 7a with a prefabricated rectangular slot 8. The regulating archwire can be applied to the slot of the internal screw. The regulating wire fits the size of the slot precisely, thus preventing its rotation after being applied. The right end 9a of the internal screw in FIG. 1 is conically tapered and after applying the regulating screw on the regulating wire supports itself on the adjacent bracket. An oblong tube-like external nut 9a of the same size is fitted onto the internal screw. Thus, the external nut engages with its internal thread the external thread of the internal screw. The end 11 of the external screw being opposite to the tapered end of the internal screw is hexagonal and has a tapered extension 12 leading to the regulating wire. This conically tapered extension supports itself against the adjacent bracket just like the tapered extension of the internal screw does.

Figure 2:
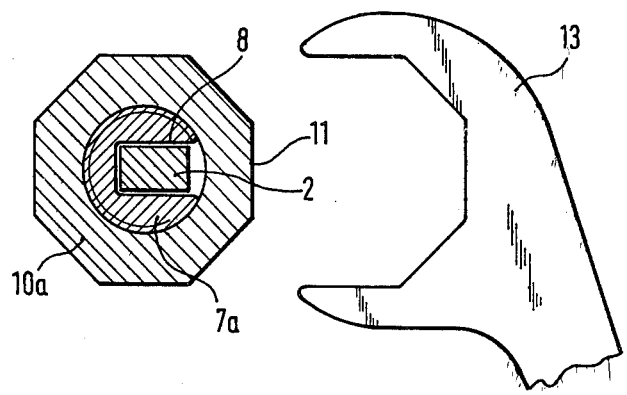
FIG. 2 is a cross-section along the line II—II in FIG. 1 together with a part of an adjustment wrench for the opening screw.

The opening screw can be adjusted with an angled wrench (hex key 13), as partly shown in FIG. 2. The precision fit of the internal screw on the regulating arch with its rectangular slot prevents rotation of the internal screw while adjusting the external nut.

Following the instructions of the orthodontist, the patient adjusts the regulating screw each week by half a turn for instance thus enlarging the length of the regulating screw according to the thread pitch of the screw. This way forces are transmitted via the brackets onto the teeth. These forces are tuned in order to prevent overload of the peridontal apparatus, but still to move the teeth slowly along the edgewise arch away from each other during a lengthy treatment time. This treatment is continued until the necessary space is opened and the malpositioned tooth can grow into the gap or be pulled into it.

Figure 3:
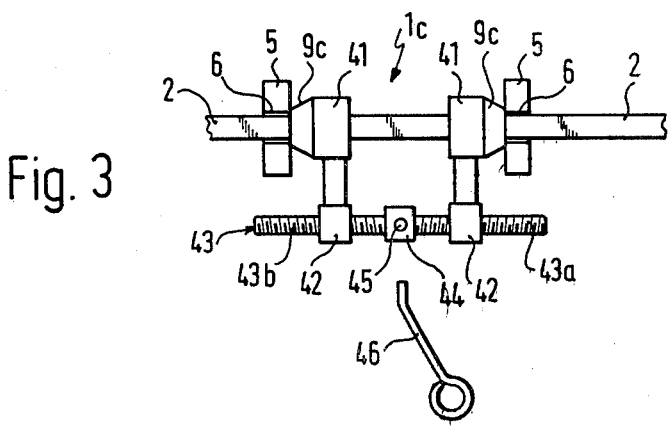
FIG. 3 is a view of another embodiment of an expansion screw according to the invention.

In FIG. 3 another opening screw 1c is shown. This regulating screw has two sliding pieces 41 to be applied on the regulating arch 2, which show conically tapered ends 9c turned towards the adjacent brackets (with their bracket arms 5). Each sliding piece is connected to a spindlenut 42 with an internal thread perpendicular to the regulating arch. The axis of the internal thread is parallel to the regulating arch. A straight thread rod 43 now screws into the internal thread of the spindle nut, the thread rod itself having a left hand thread 43a on its one side and a right hand thread 43b on the other side. The internal threads of the two spindle nuts show according shape. The middle of the thread rod is marked by an adjustment ring 44 with one or more adjustment holes 45 perpendicular to the spindle axis. The axial length of the opening screw can be adjusted by turning the thread bar. For that adjustment a little adjustment wire 46 can be inserted with its frontal end into one of the adjustment holes.

For positioning the adjustment screw on the regulating wire, first the screw will be twisted together by the use of the adjustment wire and then applied onto the regulating arch wire, which will be inserted in the bracket slots afterwards. Following this the opening screw will be unscrewed with the adjustment wire until the tapered ends of the sliding pieces touch the adjacent brackets. The patient himself then can screw the opening screw by means of the adjustment wire as instructed by the orthodontist. Once applied, parts 42, 43a 43b and 45 should come to lie in bucco-cervical areas of the oral vestibule.

The regulating screw being described in FIG. 3 can even be employed when the regulating wire is bent. For this matter, for instance, it is possible to swivel the sliding pieces to a certain extent around the spindle nuts. For specific areas of the jaws a certain curveradius of the regulating arch can be taken under consideration—by a bigger backlash of the sliding pieces on the arch—when the regulating screw is constructed.

In FIG. 4 an example of a regulating screw 1d is illustrated, in this case a contraction screw which serves the purpose to close gaps 51 between teeth 4. As stated previously, brackets 3 are bonded to the teeth and a regulating wire 2 is inserted into the bracket slots. The teeth will move towards their right position alongside said regulating arch. In this illustration the contraction screw is fastened to the bracket of the last tooth Z6 (for instance the first molar). This regulating screw has an external nut 10d shaped like a ring and is fastened to the first molar bracket so it cannot rotate. In this case the rotation is prevented by an edgewise fastening wire 52 fixed to the ring-like shaped external nut which will be inserted into an identically shaped tube 53 (auxiliary-tube) on the bracket and buckled on the other end. Such auxiliary tubes are usually already fastened to the bracket of the buccal teeth. In case none of those fastening possibilities are present, the nut can be fixed to any other fastening point or soldered onto the bracket.

Into the ring-like external nut a bar-like adjustment screw 7d with an external thread is inserted. The adjustment screw on its end opposite the external nut is provided with one or more adjustment holes 55 into which an adjustment wrench according to the adjustment wrench described in upper embodiment according to FIG. 3, can be inserted. Into the one end of the adjustment screw a holding ball 56 can be pivoted within its bearing. This ball has a pin projecting through the open bearing 55. The pin has a little eyelet 57 on its end. Through this eyelet is a ligature wire 58 or a tension wire will be drawn and led to the bracket of the tooth to be regulated in this case the upper left cuspid Z3. This wire can be fastened to the said bracket, to a little hook or an eyelet 59 of the bracket or to the wire behind the bracket. If the adjustment screw is screwed into the external nut according to the orthodontist's instructions, the tooth, in this case the upper left cuspid, will be guided along the regulating arch and the gap gradually will be closed. By connecting the tooth to which the ligature wire of the contraction screw is fastened with adjacent teeth (e.g. an 8-ligature) further teeth standing beyond the tooth to be regulated can be moved as well as be used as a support. It is not necessary that the teeth to which the tensile force is applied stand next to the gap 51.

FIG. 5 shows a part of a fixed regulating appliance with two brackets 62 consisting of a base-plate 63, bracket arm 64 and a bracket slot 65, as well as an edgewise tube 62a being fastened to the base plate 63a which are bonded to the teeth and into which an edgewise arch 66 is inserted.

Into the corner areas of the regulating arch partial threads 67 are cut which proceed for instance over an angle of a segment of approximately 30°. By this the cross-section of the regulating arch is not materially changed; especially its guiding characteristics are preserved so that the side edges fit into the bracket slot of the single brackets or the edgewise tube.

Figure 5A:
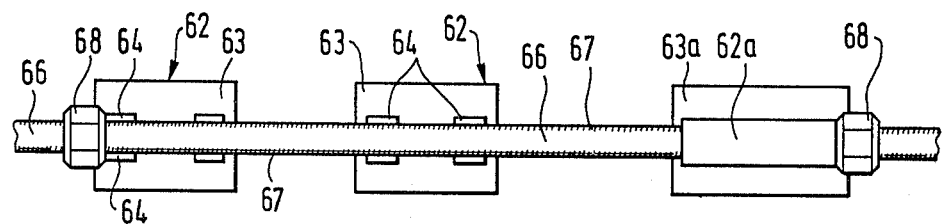
FIG. 5a is a schematic drawing of a part of a fixed regulating appliance with two integrated regulating screws according to the invention.

The thread pitch of the partial threads are cut in a way that a regulating nut 68 can be screwed completely along the partial threads of the regulating rch. The regulating nut is moved by rotation on the regulating arch and thus brought to its required position. In FIG. 5a the one regulating nut is in touch with the bracket arms of a bracket, whereas the other regulating nut contacts the one side of the edgewise tube. The regulating nuts are provided with blind holes 69 all along their external circuit into which an adjustment wrench in the shape of a pin can be inserted in order to turn the regulating nut. By adjusting the regulating nuts the brackets or the edgewise tube fastened to the regulating arch are moved. Connecting several brackets or tubes with each other (with an 8-ligature e.g.) allows movements of teeth or teeth groups even in curved parts of the regulating arch. The regulating nuts also can function as a stop on the regulating arch.

Figure 5C:
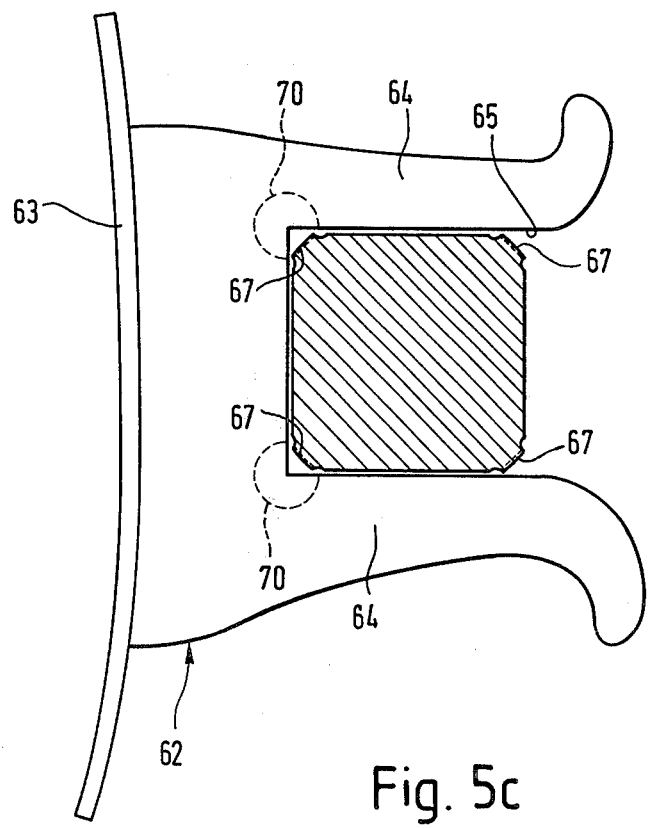
FIG. 5c is a cross-section through the regulating appliance within the region of a bracket fastened to a tooth.
Figure 5B:
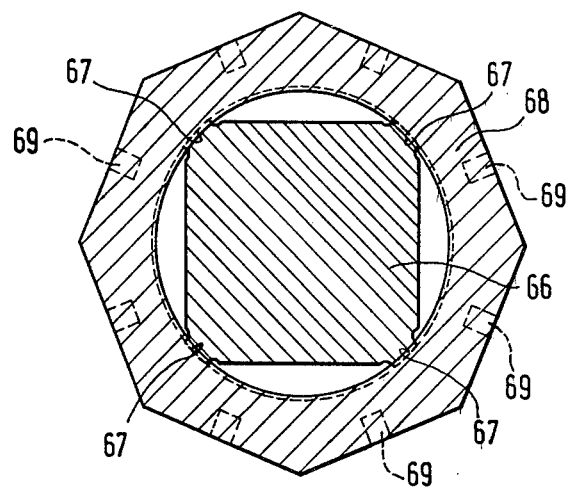
Figure 5D:
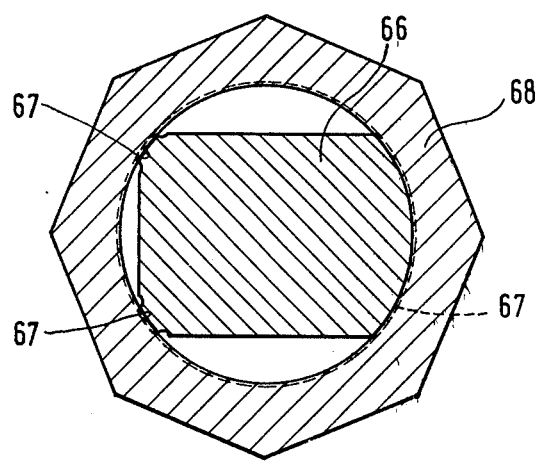
FIG. 5d is a cross-section of a further embodiment of the regulating screw similar to that of FIG. 5b with a thread in the form of a circular sector.

In FIG. 5c the broken line of the illustration shows a recess 70 in the base-plate of the bracket slot. This recess will avoid potential splining between the thread of the regulating arch and the bracket.

In FIG. 6a–6c again a part of a fixed regulating appliance is shown with a bracket 72 bonded to a tooth 81, an edgewise regulating arch 76 with partial threads 77 and a regulating nut 78. The arrangement here does not differ from the one in FIG. 5a–c. Additionally a guide shoe 82 is applied onto the regulating arch grasping the regulating wire on the other side of the bracket arms. This on the one hand avoids a splining between the partial thread of the guiding arch and the ligature wire 83 which fastens the bracket to the regulating arch and on the other hand allows an unhampered sliding of the regulating arch within the bracket slot. The guide shoe 82 consists of a slim middle part 82a of the same width as the bracket slot and two clamps 82b, one on each end, embracing the regulating arch. On their lower end the two clamps show a little notch 82c to improve its position on the regulating wire. The ligature wire is placed below the wings 74 of the bracket on both sides of the bracket and then guided over the upper side of the clamp of the guide shoe and fastened on one side. The regulating nut now is in contact with the one clamp of the guide shoe which now contacts the bracket itself. In case the ligature wire is damaged the guide shoe will not fall in the oral cavity, because it embraces the regulating arch with its two notches and thus is fastened to the arch wire.

Instead of providing each single edge of the regulating arch with a partial thread, it is enough to cut threads only in the two edges facing the base place. In this case it is suitable to provide the opposite side with a circular cross-section, the diameter of which is accordingly dimensioned to the regulating screw. The external curvature of the regulating arch can also be provided with a thread on which the regulating nut gears screw.

What I claim is:

1. A device for orthodontic regulation of the position of teeth along the curve of a jawbone comprising a fixed regulating appliance having brackets for bonding to the surface of each of said teeth, each bracket having a rectangular opening, a relatively rigid rectangular regulating archwire fixed at each end to a said bracket while being slidably guided in the openings of other said brackets, and an elongate force element supported on the regulating archwire between two of said brackets and disposed to transmit moving forces on the teeth to be regulated, the force element consisting of mating screw elements to provide adjustment of its length, the force element being fixed at its ends to two different brackets, so that by adjusting the length of the force element the teeth will be guided under control along the archwire into a desired position along said curve of said jawbone.

2. The device according to claim 1 wherein the mating screw elements comprise a nut having an internal thread and a thread fixedly associated with said regulating archwire.

3. The device according to claim 1 wherein the force element has two slidable pieces, each one rigidly connected with a threaded nut, to slidingly engage the regulating archwire, and a threaded pin, said threaded nuts and said threaded pin together forming a turnbuckle operable to adjust the distance between the two slidable pieces.

4. The device according to claim 1 wherein the screw elements comprise a threaded nut and a mating threaded pin, one of the screw elements being fastened to said bracket of the regulating appliance, the other of the screw elements being a rotatable support for tension applying means fastened to a said bracket.

5. The device according to claim 1 wherein one of the screw elements is a circumferentially interrupted thread formed on corners of the regulating archwire and the other screw element is a nut threaded to engage said interrupted thread.

6. The device according to claim 1 wherein the interrupted thread is cut into all four corners of the regulating archwire.

7. The device according to claim 5 wherein each interrupted thread spans an arc segment of approximately 30°.

8. The device according to claim 5 wherein the interrupted thread is cut into the regulating archwire only in the corners of the archwire which, in use, faces the teeth.

9. The device according to claim 8 wherein the regulating archwire has on the side lying opposite to the corners with the interrupted thread a cross section which is a sector of a circle with a diameter corresponding to the thread diameter of the nut, said sector bearing an interrupted thread to engage said nut thread.

10. The device according to claim 5 wherein a resilient guide shoe can be set on the regulating archwire adjacent said brackets of the regulating archwire adjacent said brackets of the regulating appliance in order to facilitate sliding movement between the regulating archwire and said bracket.

11. The device according to claim 10 wherein the guide shoe has a strip-like middle part as well as a clamp, to embrace the regulating archwire on each end.

* * * * *

UNITED STATES PATENT AND TRADEMARK OFFICE
CERTIFICATE OF CORRECTION

PATENT NO. : 4,483,674
DATED      : November 20, 1984
INVENTOR(S): Winfried SCHUTZ It is certified that error appears in the above-identified patent and that said Letters Patent are hereby corrected as shown below:

Claim 6, column 6, line 44, delete "1" and insert in place thereof "5".

Signed and Sealed this

Second Day of April 1985

[SEAL]

Attest:

DONALD J. QUIGG

Attesting Officer     Acting Commissioner of Patents and Trademarks